United States Patent [19]
Beretsky et al.

[11] 3,934,458
[45] Jan. 27, 1976

[54] METHOD AND APPARATUS FOR PULSE ECHO IMAGING

[75] Inventors: Irwin Beretsky, New City; Bernard Lightenstein, Yorktown Heights, both of N.Y.

[73] Assignee: Technicon Instruments Corporation, Tarrytown, N.Y.

[22] Filed: Feb. 4, 1974

[21] Appl. No.: 439,156

[52] U.S. Cl. .................................................. 73/67.9
[51] Int. Cl.² ........................................ G01N 29/00
[58] Field of Search ........................... 73/67.8, 67.9

[56] References Cited
UNITED STATES PATENTS

| | | | |
|---|---|---|---|
| 2,825,044 | 2/1958 | Peterson | 73/67.8 R |
| 3,226,535 | 12/1965 | Thompson | 73/67.8 R |
| 3,256,733 | 6/1966 | Carlin | 73/67.8 R |

OTHER PUBLICATIONS
"Attenuation Measurements Using the Pulse–Echo AB Method...." by L. C. Lynnworth From Material Evaluation, Jan. 1973, pp. 6-16.

*Primary Examiner*—James J. Gill
*Attorney, Agent, or Firm*—S. P. Tedesco; Stephen E. Rockwell; J. J. Romano, Jr.

[57] ABSTRACT

Method and apparatus are provided for processing the successive echo pulses which result from the interrogation of a layered material by energy pulses, and include the direct provision from said echo pulses of the uncompensated coherent echo response of said material to thereby preserve phase information, the provision of the compensated impulse response of said material by modification of said echo response with a non-linear correction function, and the calculation of the RAYLOGRAM of said material from said impulse response. All of the above is accomplished in the complete absence of deconvolution, and said non-linear correction function includes a normalization factor to normalize the impulse response and provision for modifying the latter to compensate for energy pulse attenuation in the material to render it more accurate by satisfying the known boundary conditions of said layered material.

22 Claims, 16 Drawing Figures

*UNIPOLAR*

*DOUBLET*

*TRIPLET*

METHOD AND APPARATUS FOR PULSE ECHO IMAGING

BACKGROUND OF THE INVENTION

1. Field of the Invention.

This invention relates to new and improved method and apparatus for the imaging of pulse echoes and is particularly adapted for use in acoustic interrogation systems for non-invasive biophysical diagnosis.

2. Description of the Prior Art.

Although a wide variety of prior art acoustic interrogation systems are available for non-invasive biophysical diagnosis, it may be understood that the same, in general will be found to be lacking in the provision of displays of good axial resolution since such systems are generally limited in operation to several cycles of transducer ring as determined by the transducer Q and the natural resonant frequency of the transducer. This is so since it is known that, for example, two boundaries separated in space by a distance S along the direction of acoustic energy propagation can only be resolved by a pulse envelope or pulse of width T when S= CT/2 where C is the velocity of propagation of the acoustic energy in the ensonified materials. In addition, although detection can be traded off in the operation of the systems of the prior art to provide increased spatial resolution in the brightness mode by raising the detection threshold level, it is believed clear that this can only be accomplished at the expense of the detection of weak echoes to therefore result in incomplete images.

Many of these prior art systems operate through use of trains of relatively uncontrolled sinusoidal energy pulses of substantial width to produce a pulse echo envelope which is representative of the modulation effects of the acoustic boundaries of the material under interrogation, and this envelope is then utilized for conventional Z axis modulation of a CRT or like display device. Envelope detection of this nature is well known by those skilled in this art to be signal processing technique that maximizes the signal to noise ratio at the expense of discarding phase detection. Thus, and although phase information based on relative acoustic impedance ratio information at said acoustic boundaries of the material under interrogation is inherent in the pulse echo signals received by these prior art devices, the same is lost through the process of envelope detection to thus significantly detract from the readability of the provided display. Too, since the prior art devices under discussion effect Z axis modulation as described in proportion to the intensity of the detected echo envelope level which exceeds a predetermined threshold, it is believed clear that such echo levels are a function not only of the impedance ratio of interest at the material boundary, but also of the attenuation of the acoustic energy due to energy absorption, spreading and the like. As a result, the brightness of the provided CRT display in such prior art devices is not representative of said impedance ratios, only, as should be obvious. Further, the use as described of trains of relatively uncontrolled sinusoidal energy pulses of substantial width by these prior art devices renders the detection of phase information from the resultant echo pulses by simple integration impossible. Also, the combination of transducer ringing and increased threshold setting as discussed hereinabove will, in biophysical interrogation applications, almost inevitably produce artifactual tissue boundaries to significant diagnostic disadvantage as should be obvious. In addition, few if any of such prior art devices are known which can automatically apply a correction for the known input and output boundary conditions of the material under interrogation.

A further significant disadvantage of some of the prior art acoustic interrogation systems resides in the fact that the same require the use of the complex mathematical procedure of echo signal deconvolution to determine the impulse response of the medium under interrogation. More specifically, it may be understood that those prior art systems which do require the use of deconvolution will most likely require the use of a relatively complex digital computer in the echo signal processing circuitry, and will be somewhat limited in the types or shapes of input waveforms that can be utilized to insure that the impulse response does not simply oscillate around zero to no useful purpose as should be obvious. Too, the use of deconvolution gives rise to the further problem that small amounts of distortion in the input waveform, as can and will generally result from signal scattering, refraction, diffraction or the like, will increase exponentially during signal processing to result in not insignificant errors in the final impedance ratio calculations.

OBJECTS OF THE INVENTION

It is, accordingly, an object of this invention to provide new and improved method and apparatus for pulse echo imaging which function to provide a pulse echo display of significantly improved readability through retention of phase information at the boundaries of the material being pulse-interrogated, and the amplitude correction of the pulse echoes to compensate for the input pressure levels of the interrogating pulses and for attenuation losses in the material to satisfy known acoustic boundary conditions.

Another object of this invention is the provision of method and apparatus as above which do not require deconvolution to accomplish echo signal processing and arrive at the impulse response of the medium under interrogation.

Another object of this invention is the provision of method and apparatus as above which utilize carefully controlled pulses of narrow width representing essentially one cycle of transducer oscillation as can be provided by very low Q transducers to thereby improve the axial resolution of the display.

Another object of the invention is the provision of method and apparatus as above which provide a pulse echo display of material interfaces or boundaries having dimensions and form which are substantially less sensitive to signal processing circuitry threshold settings.

A further object of the invention is the provision of method and apparatus as above which are particularly though not exclusively, adapted for use with acoustic energy pulses in systems for non-invasive biophysical diagnosis.

SUMMARY OF THE INVENTION

As specifically disclosed herein, the method and apparatus of the invention comprise the ensonification of a layered material with carefully controlled acoustic energy pulses which are linear derivatives of unipolar pulses; the processing of the resultant echo signals by integration or logical switching to provide the uncompensated coherent echo response of said material to ensonification as described and thereby preserve phase information regarding the relative impedances of said material layers; and the modification of said echo response to provide the compensated impulse response of the layered material to such ensonification. This impulse response is then further signal processed to provide a waveform which accurately represents the RAYLOGRAM of the respective material layer impedance ratios, and this waveform is utilized to provide a display of improved readability of said impedance ratios, with the relative brightness of the respective portions of said display being directly related to said impedance ratios. The modification of the uncompensated coherent echo response to provide the compensated impulse response comprises the application of a normalized, non-linear and readily slope-adjustable correction function to the former to render the impulse response amplitude correct and compensate for the attenuation of the ensonifying pulses in the layered material to further render said impulse response more accurately indicative of the impedance ratios of interest by satisfying known material acoustic boundary conditions. No use is made of the complex mathematical procedure of deconvolution to arrive at said compensated impulse response.

DESCRIPTION OF THE DRAWINGS

The above and other objects and advantages of this invention are believed made clear by the following detailed description thereof taken in conjunction with the accompanying drawings wherein.

DETAILED DESCRIPTION OF THE INVENTION

Essential advantageous features of the method and apparatus of the invention are that the same make use of a controlled acoustic pulse and appropriate signal processing means to extract a measure of the phase sense of the acoustic energy reflection factor $r$ at each boundary of the ensonified material, and that the same further automatically correct the amplitude levels of the reflected energy pulses by detecting pulse entry and exit conditions at each such boundary so that the thusly corrected amplitude levels are a better or more accurate measure of the pressure reflection factor $r$ at each boundary within a layered material. As a result, the amplitude of intensity of the provided display is a better or more accurate indicator of the acoustic impedance $Z_n/Z_o$ of the respective material layers separated by each boundary and the display image bears a more recognizable relationship to the ensonified region of the material under interrogation. Of particular significance is the fact that the method and apparatus of the invention do not require deconvolution in the processing of the echo signals to arrive at the echo response and the impulse response of the material under interrogation.

As specifically disclosed herein, the method and apparatus of the invention make use of a carefully controlled linear derivative of a unipolar pulse, in the nature of a doublet or triplet, to ensonify the desired material region. A unipolar pulse, and a doublet and a triplet as are linearly derived therefrom are depicted respectively at 10, 12 and 14 in FIG. 1. Preferably, the ensonification pulses are limited in width to values of about one period of the natural frequency of the pulse transmitter.

Ensonification of a layered material region by pulses of the nature depicted in FIG. 1 may be understood to produce pulse echoes, the respective phase and amplitude of which are determined by the factors discussed hereinabove. More specifically, if a unipolar pulse or linear derivative thereof produces a positive echo in passing through a material boundary wherein the acoustic impedance ratio $Z_n/Z_n-1$ of the materials which form said boundary is greater than 1, it may be understood that the same pulse will produce a negative echo in passing through a material boundary wherein said acoustic impedance ratio is less than 1, and will produce no or zero echo if said acoustic impedance ratio is equal to 1, to thus establish, for example, in the latter instance that the respective acoustic impedances, and accordingly the acoustic-mechanical or physical properties of interest of the materials which form said boundary, are the same. Further, the acoustic impedance of any medium containing the transducer relative to the acoustic impedance of any layer of a parallel layered material within the same medium is a function of the acoustic reflection factors of the material boundary layers up to the boundary of the layer of interest. Thus, and for the transducer-layered material arrangement as depicted in FIG. 2, the acoustic impedance ratio at any boundary may be readily determined in accordance with Equation (1) as follows;

Equation (1)  $\dfrac{Z_n}{Z_o} = \left(\dfrac{1+r_1}{1-r_1}\right)\left(\dfrac{1+r_2}{1-r_2}\right)\left(\dfrac{1+r_3}{1-r_3}\right)\cdots\left(\dfrac{1+r_n}{1-r_n}\right)$ where the $r_n$th reflection coefficient is related to the normalized pressure echo ($y$) as set forth in Equation (2):

Equation (2) $\quad r_n = (y_n)\left[\dfrac{e^{2\sum\limits_{i=1}^{i=n-1}\alpha_i S_i}}{\prod\limits_{i=1}^{i=n-1}(1-r_i^2)}\right]$ wherein $e$ is the base of the natural logarithm, $S$ is the distance between boundaries and $\alpha$ is the absorption factor.

Equation (2) is believed to make clear that the reflection factor $r$ can be determined by correcting the received echo pressure $y_n$ by the bracketed equation term.

In biophysical application, it may be understood that, in body tissue, the reflection factors are generally much smaller than one whereby the $r_i^2$ terms can be assumed to be zero to thus reduce the bracketed term of Equation (2) to the term of Equation (3) as follows:

Equation (3)
$$\left[ 2 \sum_{i=1}^{i=n-1} \alpha_i S_i \right]$$

wherein $S$ is the distance between layers in the ensonified material. This term of Equation (3) corrects for absorption losses.

Thus Equation (2) may be rewritten as Equation (4) as follows:

Equation (4)
$$r_n = y_{nl} \quad 2 \sum_{i=1}^{i=n-1} \alpha_i S_i$$

and this $r_n$ term of Equation (4) can be substituted in Equation (1) to determine any $Z_n/Z_o$ ratio given the appropriate $y_n$ and $n$ values for the $n$th material layer. Thus, assuming some average absorption coefficient $\bar{\alpha}$, $r_n$ can be defined as follows in Equation (5):

Equation (5)
$$r_n = y_{nl} \quad 2\alpha \sum_{i=1}^{i=n-1} S_i$$

Expanding Equation (1), for the condition $r_i \ll 1$, results in:

Equation (6)
$$\frac{Z_n}{Z_o} \approx \frac{\left[1 + \sum_{i=1}^{i=n} r_i\right]}{\left[1 - \sum_{i=1}^{i=n} r_i\right]}$$

Now it can also be seen that for small values of $\Sigma r_i$, $Z_n/Z_o$ can be further approximated as below in Equation (7):

Equation (7)
$$\frac{Z_n}{Z_o} = 2 \sum_{i=1}^{i=n-1} r_i$$

so that Equation (8) then becomes valid as follows:

Equation (8)
$$\ln \frac{Z_n}{Z_o} \approx 2 \sum_{i=1}^{i=n-1} r_i$$

Equation (6) is believed to make clear that, when the acoustic pulses enter into a layered material from a surrounding material, such as water, having an acoustic impedance $Z_o$, and exit from said layered material into the same or a somewhat different surrounding material having an acoustic impedance $Z_o$ or $Z_o'$, and where the ratio $Z_o/Z_o$ is, of course, unity, or the ratio $Z_o/Z_o'$ is known, the respective outer material boundary conditions will provide additional useful information for display as described hereinbelow.

Figure 3:
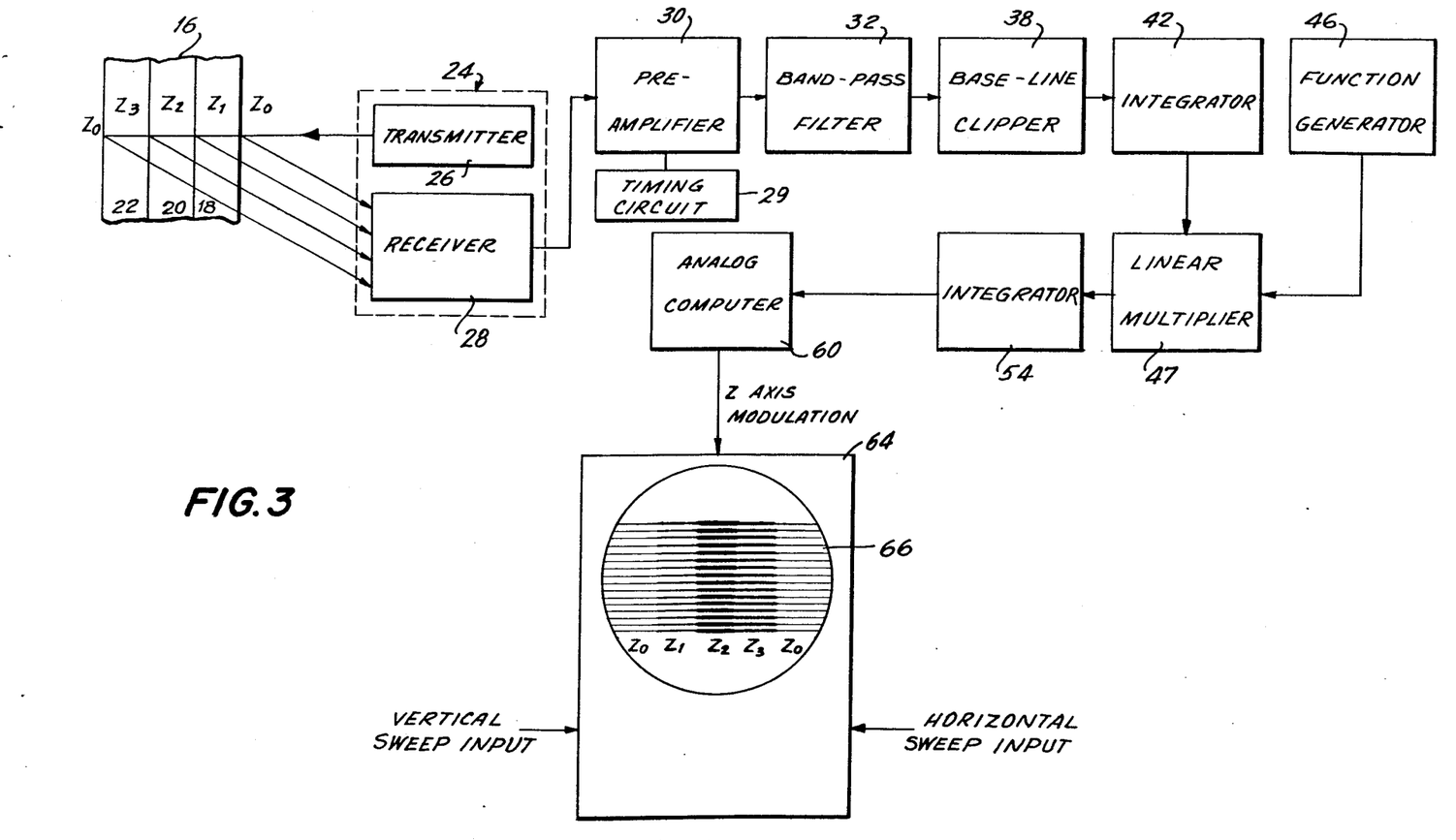
FIG. 3 is a block diagram of one embodiment of the pulse echo processing and display circuitry of the invention.

A pulse echo imaging system constructed and operative in accordance with the teachings of this invention to take maximum advantage of the above-discussed acoustical phenomena is depicted in analog block diagram form in FIG. 3 and may be understood to function to advantageously retain phase information at the respective material layer boundaries, to correct the echo level for absorption losses and other potential loss functions, and to automatically apply an appropriate correction for the known input boundary acoustic impedance $Z_o$ and the known output boundary acoustic impedance $Z_o$ or $Z_o'$.

More specifically, and referring now to FIG. 3 a layered material under acoustic interrogation is indicated generally at 16 and comprises layers 18, 20 and 22 having respective acoustic impedances $Z_1$, $Z_2$ and $Z_3$ wherein $Z_2$ is greater than $Z_1$, and $Z_3$ is less than $Z_2$. The layered material 16 is surrounded as shown by a medium which may, for example, be water and which has an acoustic impedance $Z_o$ which is smaller than $Z_1$. Under these conditions, it is believed clear that four boundaries, or lines of substantially different acoustic impedance, will be presented to the interrogating acoustic energy pulses.

Figure 1:
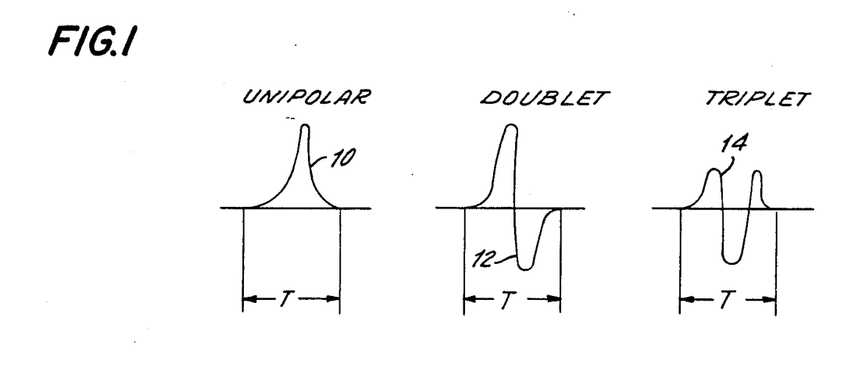
FIG. 1 is a graph depicting various types of waveforms which may be used as the interrogating pulses by the method and apparatus of the invention.
Figure 2:
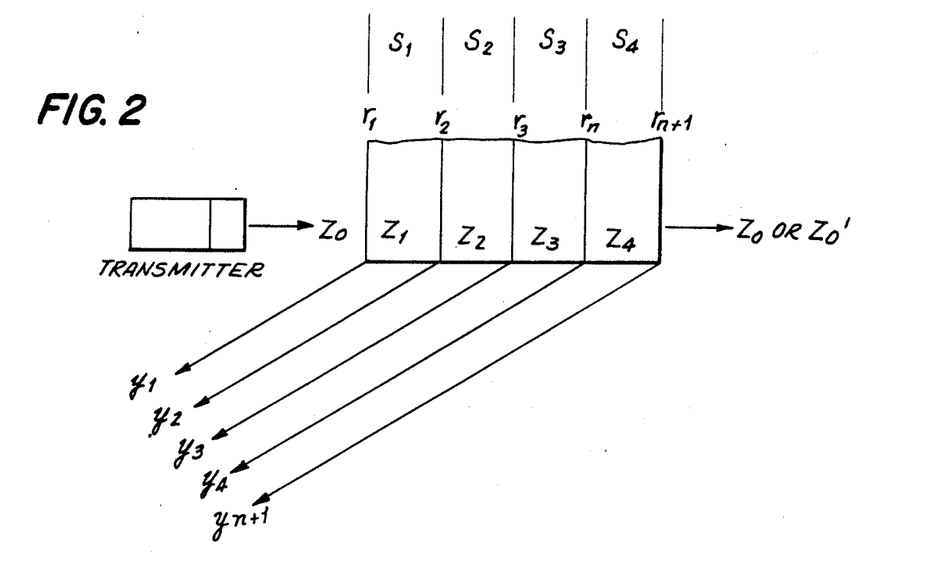
FIG. 2 depicts the interrogation of a layered material by a pulse transmitter.

A transducer is indicated generally at 24 and comprises a transmitter 26 and a receiver 28 with the former functioning to acoustically interrogate the layered material 16 with bipolar acoustic pulses of the nature depicted at 12 in FIG. 1, and the latter functioning to receive the resultant pulse echoes.

Figure 4:
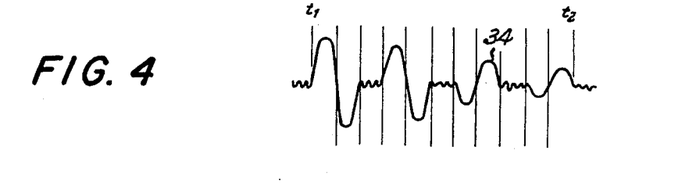
FIGS. 4 through 13, inclusive, depict the variety of waveforms that are produced by the pulse echoes as the same are processed for display by the processing circuits of the invention.

After appropriate reconversion to equivalent electrical signals in the transducer receiver, said echoes are applied as indicated to a pre-amplifier 30 for amplification, and therefore to a band pass filter 32. The echo signal leaving the pre-amplifier 30 may be assumed to be time gated by timing circuit 29 within the window $t_1-t_2$ and will take the spaced, bipolar pulse form of the waveform depicted at 34 in FIG. 4. All subsequent signal processing effected by the system of the invention may be understood to be synchronized to this $t_1-t_2$ time window.

Figure 5:
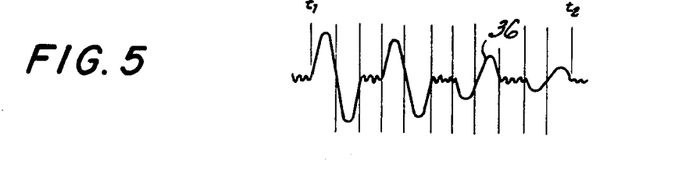

The band pass filter 32 exhibits appropriate predetermined high and low frequency roll-off characteristics which are designed to match the spectral content of the energy in the bipolar pulses of waveform 34, and functions to remove low frequency noise from the waveform 34 with maximum preservation of fidelity, with the result that the echo signal will take the form of the waveform 36 of FIG. 5 upon leaving said band pass filter.

The waveform 36 is then applied as indicated to a baseline clipper 38 which functions to remove all levels below a preset maximum allowable noise level to produce the essentially flat baseline output such as indicated by the waveform 40 of FIG. 6. Of particular significance with regard to waveform 40 is the fact that the same comprises spaced, bipolar pulses each of which includes a first-going pulse portion which clearly indicates the phase of the impedance change between the relevant material layers.

Figures 7, 8:
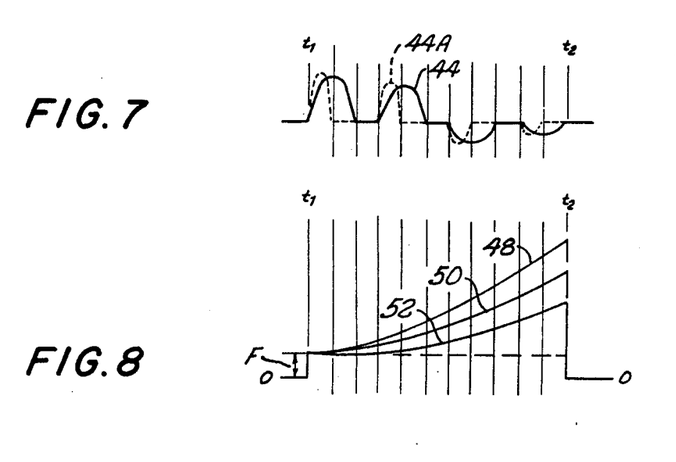

Waveform 40 is applied as indicated to integrator 42 which functions through integration to restore the pulse echo signal to unipolarity to provide the substantially noise-free waveform 44 of FIG. 7 at the output of said integrator. Waveform 44 represents the uncompensated coherent echo response of the layered material 16 to ensonification as described, and the sense or phase changes thereof may readily be seen to agree with the above-described impedance ratios in the layered material 16 and surrounding medium of FIG. 1, all as contained in the original pulse echo signal. As a result, phase information is preserved to significant advantage. Thus, in this instance, the echo response 44 may be understood to be that signal which results from bipolar ensonification and sufficient signal processing to transform the bipoles of the ensonifying energy pulses into coherent detectable impulses.

A function generator producing a waveform generally described by the bracketed term of Equation (3), and having manually adjustable slope, is indicated at 46, and a multiplier at 47, and the waveform 44 is applied as indicated from integrator 42 to said multiplier. Concomitantly, an appropriately slope-adjusted non-linear or exponential function, a representative variety of which are illustrated by the waveforms 48, 50 and 52 of FIG. 8, is applied as indicated from said function generator to said multiplier for modification of the echo response 44 in order to compensate for attenuation of the acoustic energy pulse in the layered material due to energy absorption, spreading and the like as discussed hereinabove, and thus render the ultimate pulse echo display more accurately and truly representative of the material layer impedance ratios of interest. The time period $t_1-t_2$ in FIG. 8 is equal to the time period for the reflections of the acoustical pulses to be received by receiver 28, i.e., the two-way travel time of the acoustical pulses in the layered material 16. This correction function also includes a normalization factor F which converts the amplitude of the echo response to render the resultant waveform amplitude correct, and it may be understood that this normalization factor F is determined through knowledge of the pressure levels of the ensonification pulses at the first material layer boundary of interest.

The result of the multiplication in multiplier 47 of the echo response 44 by the non-linear correction function of FIG. 8 results in the outputting of the waveform 56 from said multiplier, and said waveform 56 may readily be understood to represent the compensated impulse response of the layered material to ensonification as described. Phase information is preserved in this compensated impulse response, and it is significant that the same is arrived at in the complete absence of deconvolution.

Figure 9:
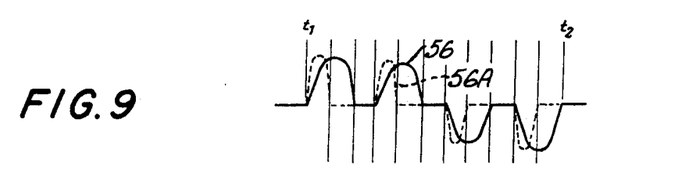
Figure 10:
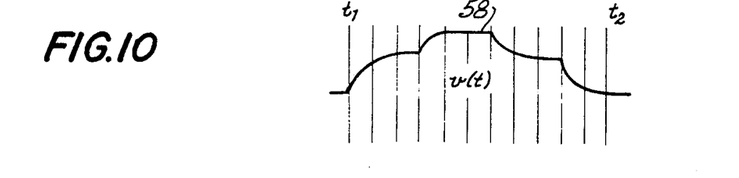

A second integrator is indicated at 54 and the impulse response waveform 56 of FIG. 9, which is provided at the output of the multiplier 47, is applied as indicated to the integrator 54 for further summation to result in the provision of the waveform 58 of FIG. 10 at the output of said integrator. Waveform 58 may be understood to represent the $\Sigma_{ri}$ term from Equation (6).

Figure 12:
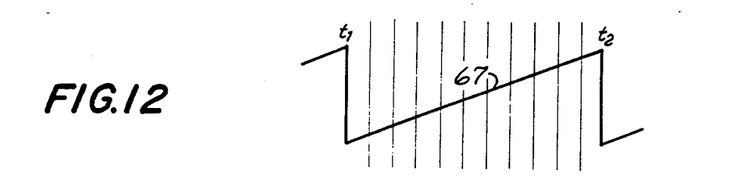
Figure 13:
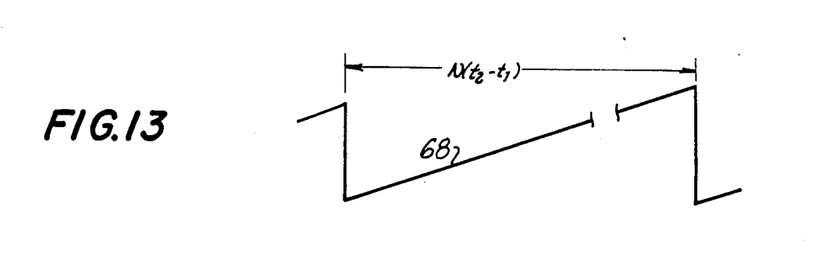

The waveform 58 is then applied to an analog computer 60 which generates the function $1+\Sigma r_i/1-Mr_i$ which fulfills Equation (6) and which is a very close approximation to the required $Z_n/Z_o$ analog. This output from analog computer 60 is illustrated as waveform 62 of FIG. 11, and this waveform is applied as indicated to an oscilloscope 64 to appropriately brighten the swept beam of the latter for use thereof in a conventional TM or B mode. Thus may be appreciated that the relative brigtness levels of the provided display will be substantially independent of threshold level settings. Horizontal and vertical sweep inputs as illustrated by the waveforms 67 and 68 of FIGS. 13 and 12 would, of course, be applied to the oscilloscope 64 as indicated to synchronize the operation thereof with the $t_1-t_2$ acoustical interrogation time window as discussed hereinabove.

The area encompassed by the waveform 62 of FIG. 11, which is called a RAYLOGRAM after the RAYL or MKS unit of acoustic impedance, represents the summation as expressed hereinabove in Equation (6) of the acoustic energy reflection coefficient $r_i$ between the limits of $i$ equal to 1 and $i$ equal to $n$, or in this case 4; while the respective levels of the waveform 62 will in turn be representative of the impedance ratio between material layer 22 and the medium, the impedance ratio between material layer 22 and the medium, the impedance ratio between material layer 20 and the medium, and the impedance ratio between material layer 18 and the medium.

Referring now to the displayed image 66 of the layered material 16 and surrounding medium on the oscilloscope 64 of FIG. 3, it may be readily seen that the respective increases in acoustic impedance between the medium and the material layers 22, 20 and 18 will be clearly indicated by the depicted increase in brightness in the apropriate areas of the correspondingly masked display, as will the substantial decrease in impedance between the material layer 18 and the medium, it being understood that increased shading in the depiction of display 66 in FIG. 3 represents increased brightness, and vice versa. It is obvious that, in the event the layer being interrogated has an impedance less than that of the medium, the brightness level corresponding to such layer would be less than the brightness level of the medium. Thus, the brightness of the display is directly related to the respective material layer impedance ratios and substantially improved readability and intelligence is provided for the display as compared, for example, with that readability provided by the displays of the acoustic interrogation systems of the prior art wherein the brightness of the display is related only to acoustic energy reflection at the material layer boundaries, with the brightness level being the same whether or not the impedance of the layer being interrogated is greater or less than that of the medium. This improved display readability and intelligence would be of very significant advantage, for example, in anatomical interrogation applications of the system of the invention by in vivo anatomical location of a body organ under interrogation through the provision of greater recognizability for soft tissue landmarks. Too, the use as described of carefully shape-controlled bipolar acoustic pulses, and the limiting of the pulse width to a narrow value of about one period of the natural frequency of the transmitter to substantially inhibit ringing of the latter, will inherently provide for higher axial resolution of the display 66 to further significant advantage as should be obvious.

Figure 14:
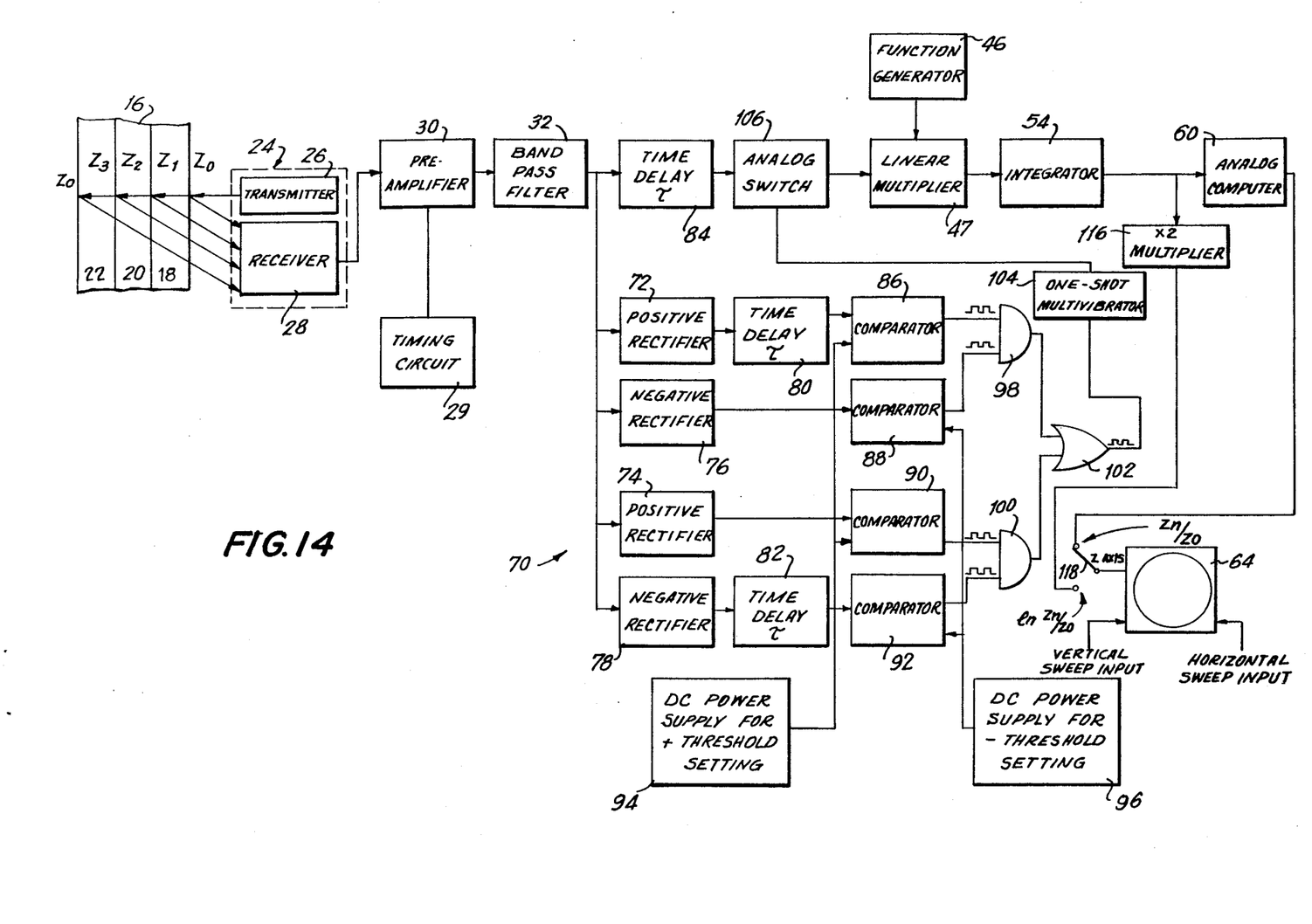
FIG. 14 is a block diagram of another embodiment of the pulse echo processing and display circuitry of the invention.

Another embodiment of the method and apparatus of the invention is depicted in block diagram form in FIG. 14 and it may be understood that like numerals identify functionally alike components in each of FIGS. 3 and 14. Thus, and with the layered material 16 again ensonified by energy pulses in the nature of the doublet 12 of FIG. 1, the waveform outputted from bandpass filter 32 in the embodiment of FIG. 14 will again be waveform 36 of FIG. 5 and will again comprise spaced bipolar pulses, the respective first-going portions of which are indicative of the phase of the change in impedance between the relevant material layers. The baseline clipper 38 of FIG. 3 is not used in the embodiment of FIG. 14 since the function thereof is performed by an analog switching circuit as described in detail directly hereinbelow.

The waveform 36 is then applied as indicated to a logical switching circuit 70 which comprises positive rectifiers 72 and 74, negative rectifiers 76 and 78, time delays 80, 82 and 84, comparators 86, 88, 90 and 92, adjustable DC power supplies 94 and 96, "and" gates 98 and 100, "or" gate 102, one shot multivibrator 104 and analog switch 106, respectively operatively interconnected as shown.

Figure 15:
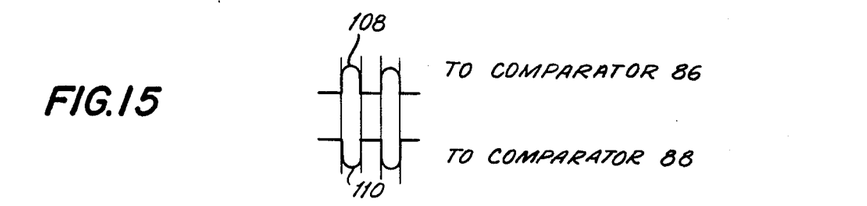
FIGS. 15 and 16 are timing diagrams drawn to the same time scale and illustrating the operation of the logical switching circuitry of the embodiment of FIG. 14.

For instances wherein the acoustical impedances of the respective material layers are increasing, or going from low to high, as indicated by the first and second bipolar pulses of waveform 40, it may be understood that the concomitant application of waveform 40 as indicated to positive rectifier 72 and negative rectifier 76, and the delay for time $\tau$ (a time equal to ½T where T is the width of the pulse transmitted by transmitter 26) of the resultant positive-going portions of said waveform, will result in the positive and negative-going portions of the first two bipolar pulses of waveform 40 respectively arriving at substantially the same time at comparators 86 and 88 as illustrated at 108 and 110 in FIG. 15. Assuming each of said positive and negative-going pulse portions to exceed the respective threshold levels as are applied to said comparators from power supplies 94 and 96, first and second pulses will be concomitantly applied from said comparators to twice enable "and" gate 98 with resultant transmission of first and second pulses therefrom through "or" gate 102 to twice turn on one-shot multivibrator 104 for appropriate time periods. This will result in the twice repeated opening of analog switch 106 with resultant transmission of the positive-going portions, only, of the first two bipolar pulses of waveform 40, as have been appropriately delayed by delay 84, through said analog switch.

Figure 16:
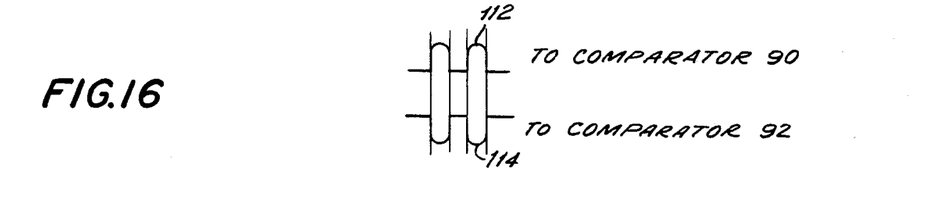

In like manner, the subsequent concomitant application of the negative and positive going portions of the third and fourth bipolar pulses of waveform 40 (which indicate in each instance that the respective impedances of the relevant material layers are decreasing or going from high to low) to positive rectifier 74 and negative rectifier 78, the subsequent delay for time $\tau$ of the resultant negative-going pulse portions from rectifier 78, and the resultant concomitant application of the positive and negative-going pulse portions to comparators 90 and 92 as illustrated at 112 and 114 in FIG. 16, will, assuming each of said pulse portions to exceed the applied threshold level, result in the concomitant application as indicated of first and second pulses from said comparators to twice enable "and" gate 100 with attendant twice repeated further opening of analog switch 106 as described hereinabove and transmission of the negative-going portions only of said third and fourth bipolar pulses through said switch. The net result of all of the above will be the appearance at the output side of analog switch 106 of the waveform 44A of FIG. 7 which again represents the uncompensated coherent echo response of the ensonified layered material 16 as is here provided by logical switching. The respective pulses of waveform 44A would each have substantially the same configuration as the corresponding pulses of waveform 44, and this similarity would include substantial coincidence of the respective leading edges of said pulses as shown. The pulses of waveform 44A would, however, be of substantially less, or roughly half, the width of the corresponding pulses of waveform 44 for reasons which should be obvious to those skilled in this art.

Figure 6:
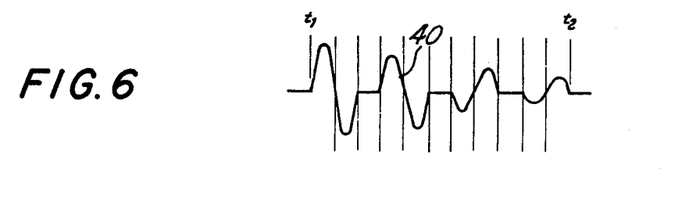

Although the above description of the logical switching circuit 70 is directed toward the operation thereof in response to a waveform such as 40 shown in FIG. 6 which comprises first and second bipolar pulses, the respective first-going portions of which are positive to indicate a decrease in impedance, it is believed made clear to those skilled in this art that said switching circuit will operate equally well in response to waveforms having other and different pulse arrangements and number.

The uncompensated coherent echo response waveform 44A of FIG. 7 is then signal processed as indicated in the embodiment of FIG. 14 by linear multiplier 47 and function generator 46 to provide the compensated impulse response waveform 56A at the output of said multiplier, and again in the absence of deconvolution. The relationship between waveforms 56 and 56A may readily be seen to be substantially the same as that described hereinabove with regard to waveforms 44 and 44A.

The waveform 56A is then signal processed in integrator 54 and analog computer 60, both of which again function as described in detail hereinabove with regard to the embodiment of a X through FIG. 3, to provide for Z axis modulation of the oscilloscope or like display device 64 and attendant display of the respective material layer impedance ratios thereon, as indicated. Alternatively, the waveform 58 of FIG. 10 which is outputted from the integrator 54 in the embodiment of FIG. 14 may be applied as indicated to X2 multiplication circuit 116 and the resultant waveform utilized, through appropriate positioning of switch 118, to provide a display of the $1n\ Z_n/Z_o$.

Figure 11:
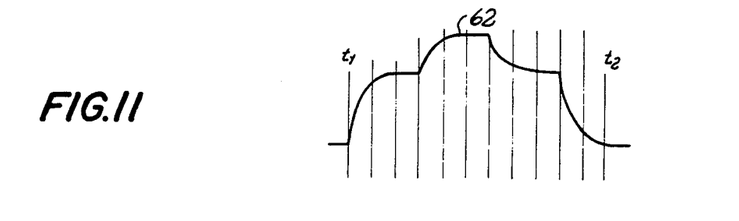

For use of the method and apparatus of the invention in applications wherein the layered material 16 of interest is bordered on both sides by a medium having the same $Z_o$ acoustic impedance, it may be understood that the oscilloscope 64 would temporarily be operated in the A scan mode and the slope of the normalized, nonlinear correction function generated by function generator 46 would be adjusted in manner as to return the displayed waveform 62 of FIG. 11 to the same level at $t_2$ as it was at $t_1$, to thus fulfill energy input and output boundary conditions and thereby accurately compensate for attenuation of the acoustic energy in the layered material 16 as discussed. Conversely, for use in applications wherein the medium to one side of the layered material 16 had a different acoustic impedance than the medium to the other side of said material, it may be understood that the slope of the generated function under discussion would be adjusted to provide a ratio level for waveform 62 at $t_2$ and $t_1$ which would correspond to the ratio of said different known impedances. Alternatively, with the oscilloscope 64 operated in the TM or B scan modes to provide the illustrated display 66, it may be understood that appropriate adjustment of the function generator 46 for instances wherein the respective impedances of the surrounding medium were equal would simply require function slope adjustment sufficient to render the spaced $Z_o$ impedance portions of the display of substantially equal brightness. Conversely, for TM or B scan mode operation wherein the respective impedances of the medium to either side of the layered material 16 were different, function slope adjustment would be effected in such manner as to provide a brightness ratio which was substantially equal to the known medium impedance ratio.

As discussed hereinabove, other linear derivatives of the unipolar pulse 10 of FIG. 1 in the nature of the triplet 14 may alternatively be used in the operation of the method and apparatus of the invention. However, it is believed clear that, for each derivative in the pulse as utilized beyond bipolarity, an additional integrator must be added to the signal processing circuitry to compensate therefor. Further, and although the generation of true unipolar pulses is known to be difficult in accordance with the current state of this art, method and apparatus in the nature, for example, of those disclosed in U.S. Pat. No. 3,656,012 are known which purport to be capable of such unipolar pulse generation. Accordingly, it is to be made clear that the respective circuit configurations of FIGS. 3 and 14 would each be well suited for use in conjunction with a transducer transmitter 26 capable of generating unipolar pulses, and that the use of such pulses for material ensonification would require substantially only change in the operational characteristics of bandpass filter 32 so that the same could perform a differentiation function on the spaced, unipolar pulse waveform which would be outputted from pre-amplifier 30 under such conditions. The waveform resultiing from such differentiation would, of course, then take the general configuration of waveform 34 in comprising spaced, bipolar echo pulses.

Of further advantage with regard to the use as described of the linear derivatives of unipolar pulses as depicted in FIG. 1, is the fact that the same enables the accurate detection of phase information through the relatively simple processes of integration or logical switching. Thus, and although acoustic interrogation devices of the prior art may utilize pre-detection integration, it may be understood that the use in said devices of sinusoidal waveforms as the interrogation pulses, of necessity results in sinusoidal waveforms no matter how many times the pulse echo signals are integrated to thus render impossible the detection of phase information by integration in said devices.

As disclosed herein, it is believed made clear that the new and improved pulse echo imaging method and apparatus of the invention would be particularly adaptable for use with eminently safe acoustic energy pulses in the non-invasive, in vivo biophysical examination and diagnosis of body organs in the nature of, for example, the heart, lungs, liver, kidneys, brain and bladder.

Although disclosed herein as operable through the use of analog pulse echo signal processing circuitry, it is believed clear that the method and apparatus of the invention could also be practiced through use of the equivalent digital pulse echo signal monitoring circuitry and appropriate A/D and D/A conversion means at the analog signal input to said circuitry, and the digital signal output thereof, respectively, to provide for suitable Z axis modulation of the oscilloscope by said pulse echo signals. One problem that might arise, however, with the use of such digital circuitry resides in the probable somewhat greater complexity and cost thereof. Too, although disclosed herein as functioning to drive an oscilloscope or like CRT device, it is believed clear that the analog signal outputted by the signal processing circuitry of the invention could equally well be utilized to drive other and different pulse echo signal display means in the nature, for example, of a strip chart recorder.

Further, although disclosed herein as operating through the use of acoustic energy pulses, it is believed clear that the method and apparatus of the invention could alternatively operate through the use of pulses of other and different forms of energy in the nature, for example, of electrical energy, so long as the same will provide suitable pulse echoes for processing and display.

While we have shown and described the preferred embodiment of our invention, it will be understood that the invention may be embodied otherwise than as herein specifically illustrated or described, and that certain changes in the form and arrangement of parts and in the specific manner of practicing the invention may be made without departing from the underlying idea or principles of this invention within the scope of the appended claims.

What is claimed is:

1. A method for pulse echo processing comprising, the steps of, interrogating a layered material with energy pulses of controlled waveform, receiving the pulse echoes which result from the interrogation of said layered material, operating upon said pulse echoes to provide a pulse echo waveform comprising a plurality of echo pulses, each of said echo pulses including a pulse portion which indicates the phase of the change in impedance, if any, between said material layers, generating the echo response of said layered material to said energy pulses from said pulse echo waveform to thereby preserve said phase change indications, generating the impulse response of said layered material by compensating said echo response to satisfy at least two known impedance conditions of said layered material, and further processing said impulse response to produce a quantitative display of the relative impedances of said layered material.

2. A method as in claim 1 wherein, the generation of said echo response comprises the integration of said pulse echo waveform.

3. A method as in claim 1 wherein, the generation of said echo response comprises the selection of said echo pulse portions, only.

4. A method as in claim 1 wherein, said energy pulses are linear derivatives of unipolar pulses.

5. A method as in claim 1 wherein said echo pulses are spaced, multi-polar pulses and the generation of the echo response of said layered material comprises, the steps of, comparing the respective positive and negative going portions of each of said multi-polar pulses with respective positive and negative threshold levels, and selecting only said pulse portions which indicate the phase of the impedance change.

6. A method as in 1 wherein, the generation of said impulse response comprises the application of a non-linear correction function to said echo response to normalize the amplitude level thereof and compensate for the attenuation of said energy pulses in said layered material by satisfying the known acoustic boundary conditions of said layered material.

7. A method as in claim 6 wherein, said non-linear correction function is an exponential function, the slope of which is adjustable in accordance with the relationship between said known acoustic boundary conditions of said layered material.

8. A method as in claim 1 further comprising, the steps of, calculating the impedance ratio of said material layers from said impulse response.

9. A method as in claim 8 wherein, the calculation of said impedance ratio comprises the integration of said impulse response to provide a waveform which represents the term $\Sigma\, r_i$, wherein $r_i$ is the acoustic energy reflection coefficient at each layered material boundary, and the modification of said waveform by a function which very closely approximates the term $1+\Sigma\, r_i/1 - Mr_i$ to thereby provide the RAYLOGRAM of said layered material.

10. Apparatus for pulse echo processing comprising, means for interrogating a layered material with energy pulses of controlled waveform, means for receiving the pulse echoes which result from the interrogation of said layered material and providing a pulse echo waveform comprising a plurality of echo pulses in response thereto, each of said echo pulses including a pulse portion which indicates the phase of the change in impedance, if any, between said material layers, means for generating the echo response of said layered material to said energy pulses from said pulse echo waveform to thereby preserve said phase change indications, means for generating the impulse response by compensating said echo response to satisfy at least two known impedance conditions of said layered material, and means responsive to said last mentioned means to provide a quantitative display of the relative impedances of said layered material.

11. Apparatus as in claim 10 wherein, said means to generate the echo response comprise integration means for integrating said pulse echo waveform.

12. Apparatus as in claim 10 wherein, said means to generate said echo response comprise means to select said echo pulse portions, only.

13. Apparatus as in claim 10 wherein, said interrogating means are operable to generate linear derivatives of unipolar pulses.

14. Apparatus as in claim 10, wherein said echo pulses are spaced, multi-polar pulses and said means for generating said echo response comprise, means for comparing the respective positive and negative going portions of each of said multi-polar pulses with respective positive and negative threshold levels, switch means for controlling the transmission of said pulse portions, and means operatively connected to said comparison means for controlling said switch means to transmit only said pulse portions which are indicative of the phase of the impedance change.

15. Apparatus as in claim 10 wherein, said means for generating said impulse response comprise function generator means to generate a non-linear correction function for normalizing the amplitude level of said echo response to compensate for the attenuation of said energy pulses in said layered material by satisfying the known acoustic boundary conditions of said layered material, and means to apply said function to said echo response.

16. Apparatus as in claim 15 wherein, said non-linear correction function is an exponential function, the slope of which is adjustable in accordance with the relationship between said known acoustic boundary conditions of said layered material.

17. Apparatus as in claim 10 further comprising, means for calculating the impedance ratio of said material layers from said impulse response.

18. Apparatus as in claim 17 wherein, said means for calculating the impedance ratio of said material layers from said impulse response comprise, means for integrating said impulse response to provide a waveform which represents the term $\Sigma r_i$, wherein $r_i$ is the acoustic energy reflection coefficient at each layered material boundary, means to generate a function which very closely approximates the term $1+\Sigma r_i/1-Mr_i$, and means to apply said function to said waveform to provide the RAYLOGRAM of said layered material.

19. A method for pulse echo processing comprising, the steps of, receiving the train of echo pulses which result from the interrogation of a layered material with energy pulses of controlled waveform which are linear derivatives of unipolar pulses and the detection of said reflected energy pulses from the boundaries of said material layers, and processing said train of echo pulses in the absence of deconvolution to provide the impulse response of said layered material by compensating said reflected energy pulses for energy losses in said layered material.

20. A method as in claim 19 wherein, the processing of said echo pulse train comprises, the application of a non-linear correction function to said echo pulse train to normalize the amplitude level thereof and compensate for the attenuation of said energy pulses in said layered material by satisfying the known acoustic boundary conditions of said layered material.

21. Apparatus for pulse echo processing comprising, means for receiving the train of echo pulses which result from the interrogation of a layered material with energy pulses of controlled waveform which are linear derivatives of unipolar pulses and the detection of said reflected energy pulses from the boundaries of said material layers, and means for processing said train of echo pulses in the absence of deconvolution to convert the same into the impulse response of said layered material by compensating said energy pulses for energy losses in said layered material.

22. Apparatus as in claim 21, wherein, said means to process said echo pulse train comprise, means to generate a non-linear correction function to normalize the amplitude level of said pulse train and compensate for the attenuation of said energy pulses in said layered material by satisfying the known boundary conditions of said layered material, and means to apply said correction function to said echo pulse train.

\* \* \* \* \*